United States Patent [19]

Stoner et al.

[11] Patent Number: 5,453,375

[45] Date of Patent: Sep. 26, 1995

[54] METHOD AND COMPOSITIONS FOR THE DEGRADATION OF TRIBUTYL PHOSPHATE IN CHEMICAL WASTE MIXTURES

[75] Inventors: Daphne L. Stoner, Idaho Falls, Id.; Albert J. Tien, Zurich, Switzerland

[73] Assignee: Lockheed Idaho Technologies Company, Idaho Falls, Id.

[21] Appl. No.: 108,345

[22] Filed: Aug. 18, 1993

[51] Int. Cl.[6] .................... B09B 3/00; C12N 1/12; C12N 1/38; C02F 3/00
[52] U.S. Cl. .................. 435/262.5; 435/262; 435/252.1; 435/244; 210/601; 210/620
[58] Field of Search ................. 435/262, 262.5, 435/252.1, 244; 210/601, 620

[56] References Cited

U.S. PATENT DOCUMENTS

| | | | |
|---|---|---|---|
| 4,664,805 | 5/1987 | Focht | 210/611 |
| 4,808,535 | 2/1989 | Isbister | 435/252.1 |
| 4,992,174 | 2/1991 | Caplan et al. | 210/610 |

OTHER PUBLICATIONS

Kawai et al. Chemical Abstracts CA107(4):28119x 1985.
Kawai et al. Chemical Abstracts CA108(16):137493f 1986.
Kawai et al. JICST-E Abstract 890216880 1988.
Daley, R. J. et al., "Direct counts of aquatic bacteria by a modified epifluorescence technique", Limnol. Oceanogr., 20:875–882 (1975).
Doetsch, R. N., "Specimen preparation for light microscopy", pp. 21–33, as presented in P. Gerhardt (ed.), *Manual of Methods for General Bacteriology*, American Society for Microbiology, Washington, D.C. (1981).
Fedorak, P. M. et al., "Microbiol degradation of alkyl carbazoles in Norman Wells crude oil", *Appl. Environ. Microbiol.*, 47:858–862 (1984).
Horowitz, B., "Investigations into the application of tri(n-butyl)phosphate/detergent mixtures to blood derivatives", pp. 83–96 (1989), as presented in J. Morgenthaler (ed.), *Virus Inactivation in Plasma Products. Current Studies in Hematology and Blood Transfusion.*, vol. 56, S. Karger, Basel, Switzerland.
Jones, C. J. et al., Chapter 2 entitled "Miscellaneous industrial uses", pp. 81–141, as presented in W. W. Schulz et al. (eds.), *Science and technology of tributyl phosphate*, vol. II; Part B, CRC Press, Inc., Boca Raton, Fla. (1987).
Peterson, G. L., "A simplification of the protein assay method of Lowery et al which is more generally applicable", *Analytical Biochem.*, 83:346–356 (1977).
Kawai, S. et al., "Degradation of organophosphoric acid triesters by the bacteria in the river water of Osaka City", *Ann. Report of Osaka City Institute of Public Health and Environmental Sciences*, 48:175–183 (1986).
Rosenberg, A. et al., "Microbial cleavage of various organophosphate insecticides", *Appl. Environ. Microbiol.*, 37:886–891 (1979).
Kawai, S. et al., "Degradation of organophosphoric acid triesters by the bacteria in the river water (II)–Properties of TBP degrading bacteria and their enzymes", *Ann. Report of*

(List continued on next page.)

Primary Examiner—Michael G. Wityshyn
Assistant Examiner—T. J. Reardon
Attorney, Agent, or Firm—Klaas Law O'Mera & Malkin; Alan D. Kirsch

[57] ABSTRACT

A method and process for the degradation of tributyl phosphate in an organic waste mixture and a biologically pure, novel bacteria culture for accomplishing the same. A newly-discovered bacteria (a strain of Acinetobacter sp. ATCC 55587) is provided which is combined in a reactor vessel with a liquid waste mixture containing tributyl phosphate and one or more organic waste compounds capable of functioning as growth substrates for the bacteria. The bacteria is thereafter allowed to incubate within the waste mixture. As a result, the tributyl phosphate and organic compounds within the waste mixture are metabolized (degraded) by the bacteria, thereby eliminating such materials which are environmentally hazardous. In addition, the bacteria is capable of degrading waste mixtures containing high quantities of tributyl phosphate (e.g. up to about 1.0% by weight tributyl phosphate).

17 Claims, 6 Drawing Sheets

OTHER PUBLICATIONS

Osaka City Institute of Public Health and Environmental Sciences, 49:160–166 (1987).

Saeger, V. W. et al., "Environmental fate of selected phosphate esters", *Environ. Sci. Technol.*, 13:840–844 (1979).

Kawai, S. et al., "Degradation of organophosphoric acid triesters by the bacteria in the river water (III)–Immobilization of TBP degrading bacteria", *Ann. Report of Osaka City Institute of Public Health and Environmental Sciences*, 50:100–105 (1987).

Zosim, Z. et al., "Uranium binding by emulsan and emulsanosols", *Biotechnol. Bioeng.*, 4 25:1725–1735 (1983).

Michel, L. J. et al., "Cadmium accumulation by immobilized cells of a *Citrobacter* sp. using various phosphate donors", *Biotechnology and Bioengineering*, 28:1358–1365 (1986).

Smibert, R. M. et al., Chapter 20 entitled "Manual of Methods for General Bacteriology", American Society for Microbiology, Washington, D.C. (1981).

Swanson, J. L., "PUREX process flowsheets", pp. 55–79, as presented in W. W. Schulz et al. (eds.), *Science and technology of tributyl phosphate, vol. III*, CRC Press, Inc., Boca Raton, Fla. *(1990)*.

Tien, A. J. et al., "Growth of microbial cultures on tributyl phosphate", Abstract, 91st Annual Meeting American Society for Microbiology, May 5–9, 1991, Dallas, Tex., p. 262.

Macaskie, L. E., "The application of biotechnology to the treatment of wastes produced from the nuclear fuel cycle: Biodegradation and bioaccumulation as a means of treating radionuclide–containing streams", *Critical Reviews in Biotechnology*, 11:41–112 (1991).

METHOD AND COMPOSITIONS FOR THE DEGRADATION OF TRIBUTYL PHOSPHATE IN CHEMICAL WASTE MIXTURES

CONTRACTUAL ORIGIN OF THE INVENTION

The United States Government has rights in this invention pursuant to Contract No. DE-AC07-76ID01570 between the U.S. Department of Energy and EG&G Idaho, Inc. now Contract No. De-AC07-94ID13223 between the U.S. Department of Energy and Lockheed Idaho Technologies Company.

BACKGROUND OF THE INVENTION

The present invention generally relates to the treatment of hazardous chemical wastes, and more particularly to the degradation of tributyl phosphate in organic chemical waste mixtures using a novel, newly-discovered strain of bacteria. Acinetobacter genospecies 11 (ATCC 55587). A deposit of the microorganism has been made in the American Type Culture Collection, Rockville, Md. on Jun. 10, 1994, and is available under conditions set forth in 37 CFR. Throughout this specification the terms Acinetobacter sp. ATCC 55587, Acinetobacter BGL1a and Acinetobacter genospecies 11 are used alternatively to refer to the same organism.

The effective treatment of hazardous chemical waste materials is of considerable importance for numerous reasons. Primarily, the health, safety, and welfare of the general public is of greatest concern. In accordance with this fact, increasingly strict local and national regulations have been enacted which relate to chemical pollution involving virtually all types of industrial waste. One chemical material of recent concern involves a material known as tributyl phosphate (hereinafter "TBP") which has the following chemical structure:

$(C_{12}H_{27}O_4P)$

TBP is primarily used throughout the world as an extractant for the processing and recycling of nuclear fuel materials as described in *Science and Technology of Tributyl Phosphate*, Vol. III, CRC Press, Boca Raton, Fla., edited by Schulz, W. W., et al. (article therein entitled "Purex Process Flowsheets", pp. 55–79 (1990) by Swanson, J. L.). Typically, odorless kerosenes, alkane mixtures, and/or chlorinated alkanes are combined with TBP as diluents when TBP is used as a nuclear fuel processing agent. TBP also has other uses, including but not limited to use as a plasticizer, hydraulic fluid, herbicide, insecticide, an extractant for rare earth metals, a catalyst, a corrosion inhibitor, and as an antimicrobial/thermal decomposition resistivity additive in petroleum-based hydraulic fluids and cutting oils (see *Science and Technology of Tributyl Phosphate*, Vol. II, CRC Press, Boca Raton, Fla., edited by Schulz, W. W., et al. (article therein entitled "Miscellaneous Industrial Uses", pp. 81–141 (1987) by Jones, C. J., et al.). TBP has even been used to deactivate the human immunodeficiency virus (HIV) during blood fractionation as noted in *Current Studies in Hematology and Blood Transfusion*, Vol. 56, S. Karger, Basel, Switzerland (article therein entitled "Investigations into the Application of Tri(n-butyl) Phosphate/Detergent Mixtures to Blood Transfusions", pp. 83–96 (1989) by Horowitz, B.). Accordingly, there are many important uses for TBP in a wide variety of technical fields. However, TBP waste materials are primarily generated in the nuclear fuels processing industry in the form of oily mixed liquid wastes containing a wide variety of organic materials including but not limited to dodecane, tridecane, tetradecane, pentadecane, kerosene, turbine oil, chlorinated alkanes, and others. These mixed waste materials may also include radioactive waste compounds therein. For example, it was estimated that about 6 million gallons per year of aqueous TBP and radioactive mixed waste materials were being generated from nuclear fuel processing operations at Hanford, Wash. (U.S.A.) which is a primary U.S. Government nuclear fuel processing facility. As a result, significant problems exist regarding the disposal of these materials in a safe and effective manner.

The importance of effectively treating/handling TBP and TBP-containing mixed wastes is characterized by numerous adverse side-effects experienced by humans coming in contact with these materials. For example, TBP is considered a hazardous material in that it is harmful if inhaled, ingested, or absorbed through the skin. TBP vapor is highly irritating to the eyes, nasal mucosa, and upper respiratory tract. It specifically causes skin irritation and nausea. While the long-term effects of TBP exposure are not entirely understood at present, it is assumed that TBP exposure can generally cause damage to the human central nervous system. In addition, it should be noted that the organic materials (e.g. long-chain chlorinated and non-chlorinated alkanes) usually combined with TBP in the above-described mixed liquid waste materials may also be considered environmentally hazardous.

Typically, organic mixed liquid wastes containing TBP are stored in metal tanks and drums which are either above-ground or buried underground. In either case, if the integrity of these tanks or drums is compromised through deformation, corrosion, or the like, considerable environmental problems can result. For example, the escape of mixed organic liquid wastes containing TBP from above-ground tanks and drums can cause a variety of adverse effects with respect to human and animal life as described above. Regarding underground tanks and drums, the leakage of TBP-containing waste materials can cause ground water/soil contamination as the waste materials percolate, migrate, and diffuse through the soil.

In an attempt to solve these problems, conventional waste treatment methods have been used in connection with TBP-containing mixed organic wastes. These traditional methods include: (1) incineration; (2) adsorption onto solid media (e.g. activated carbon); and (3) concentration by evaporation and further storage of the concentrated product. However, all of these methods either generate further polluting wastes or do not physically eliminate the organic chemical agents of concern. Also, they typically involve considerable expense and frequently encounter objections by the general public (e.g. with respect to incineration and the by-the general public (e.g. with respect to incineration and the by-products generated therefrom).

Accordingly, prior to development of the present invention, a long-felt need existed for an effective and permanent process designed to eliminate TBP (and other organic wastes combined therewith) from liquid waste mixtures. The present invention satisfies this need in a highly effective and efficient manner as described below.

SUMMARY OF THE INVENTION

It is an object of the present invention to provide a method for efficiently treating liquid waste mixtures containing TBP and various other organic constituents wherein the TBP and organic constituents are effectively degraded.

It is another object of the invention to provide a method for degrading TBP and other organic constituents in a liquid waste mixture which is rapid, highly effective, cost-efficient, and environmentally sound.

It is another object of the invention to provide a method for degrading TBP and other organic constituents in a liquid waste mixture which uses a unique, newly-discovered bacteria that metabolizes these materials so that they may be substantially eliminated.

It is a further object of the invention to provide a biologically pure culture of a newly-discovered bacterial organism (an Acinetobacter sp. designated by the inventors as strain "BGL1a") which is capable of degrading TBP and other organic constituents in a liquid waste mixture.

It is a still further object of the invention to provide a bioreactor system wherein the above-listed organism is combined with liquid waste materials containing TBP and other metabolizable organic constituents so that the TBP and organic constituents may be metabolized (degraded).

It is an even further object of the invention to provide a bioreactor system using the above-described organism wherein the organism is capable of treating liquid waste materials containing relatively high quantities of TBP (e.g. up to about 1.0% by weight) so that the TBP is effectively degraded.

In accordance with the foregoing objects, the present invention involves a highly efficient and environmentally sound method for treating liquid waste mixtures containing TBP in combination with various organic waste materials. As noted above, such waste mixtures are typically generated in the processing of nuclear fuels and involve a wide variety of organic components including but not limited to alkanes (e.g. dodecane), chlorinated hydrocarbons, petroleum-based oils, and various other materials. To substantially eliminate these materials (especially TBP) from the foregoing liquid waste mixtures, the present invention involves a bioremediation process in which a special bacterial organism is mixed with the waste materials. In a preferred and optimum embodiment, this is accomplished using a newly-discovered bacteria (a strain of Acinetobacter sp. ATCC 55587). For the purposes of this invention and for the sake of convenience, this organism shall hereinafter be designated as "Acinetobacter sp. ATCC 55587". As described below, Acinetobacter sp. ATCC. 55587 is capable of metabolizing (degrading) TBP and organic wastes combined therewith in a safe, effective, and efficient manner.

To implement the process of the present invention, a biologically pure culture of Acinetobacter sp. ACCT 55587 bacteria is first obtained in a manner described in greater detail below. Basically, Acinetobacter sp. ATCC 55587 bacteria may be found in soil materials contaminated with petroleum products. Tests have demonstrated that Acinetobacter sp. ATCC 55587 bacteria can effectively metabolize (degrade) commercial petroleum-based oil products composed of heavy dewaxed paraffinic alkanes, notwithstanding the presence of additional materials combined therewith including but not limited to antioxidants and rust inhibitors. Acinetobacter sp. ATCC 55587 was first isolated from oil-contaminated soil at a specific location in Idaho Falls, Id. (U.S.A.) as further identified and discussed in greater detail below.

After isolating the bacteria and obtaining a pure culture thereof, the organism is added to liquid waste materials containing TBP in combination with various other organic compounds including but not limited to dodecane, tridecane, tetradecane, pentadecane, n-butanol, kerosene, turbine oil, and mixtures thereof. All of these materials are capable of being used as a growth substrate by Acinetobacter sp. ATCC 55587. In most cases, the process of the present invention will be highly effective in treating liquid waste mixtures containing up to about 10.0% by weight combined non-TBP metabolizable organic compounds, and up to about 1.0% by weight TBP. A unique aspect of the present invention and the use of Acinetobacter sp. ATCC 55587 bacteria is the ability of this organism to degrade waste mixtures containing substantial quantities of TBP (e.g. up to about 1.0% by weight TBP and possibly more).

In a waste mixture containing the above-listed quantities of contaminants, Acinetobacter sp. ATCC 55587 bacteria is preferably added to the mixture in an amount equal to about $10^5$–$10^8$ Acinetobacter sp ATCC 55587 bacterial cells per ml of liquid waste mixture. However, the amount of Acinetobacter sp. ATCC 55587 bacteria to be used will vary, depending on the relative concentrations of contaminants in the liquid waste mixture. After combining the Acinetobacter sp. ATCC 55587 bacteria with the liquid waste mixture, the bacteria/waste mixture combination is agitated and allowed incubate for about 10–30 days at a sustained temperature of about 20°–30° C. After termination of the foregoing incubation period, the Acinetobacter sp. ACTT 55587 bacteria will have co-metabolized (degraded) the TBP and other metabolizable organic compounds associated therewith in the waste mixture. Specifically, through metabolic processes which are not yet entirely understood, the Acinetobacter sp. ATCC 55587 bacteria is capable of effectively eliminating approximately 50–95% of the TBP and about 95–100% of the organic co-contaminants (e.g. those materials which the bacteria is able to use as growth substrates) in waste mixtures having the composition characteristics set forth above. While the biological mechanisms used by Acinetobacter sp. ACTT 55587 bacteria to accomplish degradation of the foregoing materials are currently unknown, it is understood that such materials are cometabolized as noted above. The term "co-metabolized" as used herein shall involve a situation wherein a material which is not utilized for growth by an organism can, in fact, be metabolized when combined with another material which is a growth substrate for the organism. Specifically, in the present case, TBP is not effectively metabolized by Acinetobacter sp. bacteria unless it is combined with other organic materials which the bacteria can use as growth substrates. Thus, the use of Acinetobacter sp. ACTT 55587 bacteria is of primary importance in situations involving mixed TBP waste materials which are normally the type of wastes encountered in most industrial TBP-based applications. As far as degradation of the foregoing materials by Acinetobacter sp. ATCC 55587 bacteria is concerned, the term "degradation" as used herein shall involve a situation wherein the TBP and organic co-contaminants associated therewith are converted by the bacteria to cell mass (e.g. bacterial cellular components), fatty acids, acetic acid, and the like. These materials are essentially non-hazardous and may be released into the environment or stored with a minimal degree of risk.

In a preferred embodiment, the biological degradation of TBP and its associated organic co-contaminants by Acinetobacter sp. ACTT 55587 bacteria will occur within a specific bioreactor system consisting of a containment vessel designed to retain a supply of the bacteria and mixed liquid wastes to be treated. The size of this vessel will vary, depending on the desired amount of waste materials to be treated. The containment vessel will further include agitation means associated therewith for effectively agitating the liquid waste mixture and combined Acinetobacter sp. bacteria. While a wide variety of different agitation systems may be used in connection with the present invention, a preferred agitation system for the purposes set forth herein will consist of a conventional impeller, motorized rotating blade system, or other forced circulation apparatus known in the art. In addition, the containment vessel will further include temperature control means associated therewith to maintain the combined Acinetobacter sp. bacteria and liquid waste mixture at a preferred sustained temperature of about 20°–30° C. as noted above. While many different temperature control systems may be used, a preferred temperature control system will consist of a conventional temperature probe (e.g. thermistor) coupled with a standard setpoint controlled heating system. It should be noted that the selected temperature control system should be operated so that the temperature of the bacteria and liquid waste mixture will preferably not exceed about 35° C. Otherwise, bacterial cell death may occur.

The bioreactor system described herein may further include two additional (optional) subsystems. First, the bioreactor system may include oxygenation means operatively connected to and in fluid communication with the containment vessel. The oxygenation means is designed to supply an oxygen-containing gas (e.g. pure oxygen or air) to the combined Acinetobacter sp. bacteria and liquid waste mixture. Because the bacteria is an aerobic organism (e.g. an aerobic gram negative rod), the presence of sufficient quantities of oxygen is desirable and necessary for bacterial growth and metabolic activity. While many different types of oxygenation systems may be used, an exemplary oxygenation means will consist of a plurality of commercially-available tubular membranes inserted within the bacteria/waste combination in the containment vessel. An oxygen-containing gas (e.g. air or pure oxygen) is then supplied to the membranes which will subsequently diffuse therethrough in a substantially bubble-free manner. Alternatively, in order to oxygenate the bacteria/waste combination in the containment vessel, a selected oxygen-containing gas (e.g. pure oxygen or air) may simply be introduced into the head space within the vessel or pumped directly into the bacteria and liquid waste materials.

Second, the bioreactor system of the present invention may include pH control means operatively connected to and in fluid communication with the containment vessel for adjusting and controlling the pH of the combined Acinetobacter sp. bacteria and liquid waste mixture. In a preferred embodiment, the pH of these combined materials is optimally maintained at about 6.5–8.5. Proper pH adjustment within this range is desired and appropriate in order to maintain bacterial viability. While numerous conventional pH control systems may be used in connection with the bioreactor system described herein, an exemplary and preferred system for this purpose shall involve a conventional pH probe coupled to a set point control system which will activate standard acid or base dispensing systems as needed.

In addition, buffers may also be added to the combined materials within the containment vessel in order to moderate and control pH levels. Further information regarding the foregoing bioreactor system and the components/operational features associated therewith will be provided below.

In summary, the present involves a unique and highly-efficient method for degrading TBP and organic co-contaminants associated therewith in a liquid waste mixture. The degradation of these components is accomplished biologically using a newlydiscovered bacteria designated herein as Acinetobacter sp. ATCC 55587. This organism not only effectively degrades the foregoing materials, but it accomplishes degradation in a cost-effective, environmentally sound manner using minimal amounts of complex equipment and materials. Thus, the present invention represents a true advance in the art of waste treatment. These and other objects, features, and advantages of the invention shall be described below in the following Brief Description of the Drawings and Detailed Description of Preferred Embodiments.

DETAILED DESCRIPTION OF PREFERRED EMBODIMENTS

As described in detail herein, the present invention involves a unique and highly-efficient method for degrading tributyl phosphate ("TBP") and a wide variety of organic compounds combined therewith in a liquid waste mixture. The environmental and toxicity problems associated with TBP are indicated above. Also, as previously noted, waste TBP is most commonly found in combination with radioactive materials and non-TBP organic compounds in liquid waste mixtures. Such mixtures are typically produced in the nuclear fuels processing industry. Exemplary organic compounds normally found in combination with TBP in liquid waste mixtures include but are not limited to dodecane, tridecane, tetradecane, pentadecane, n-butanol, kerosene, petroleum-based oils, and mixtures thereof. While the present invention shall be described herein with primary reference to the foregoing organic compounds, the process of the invention is prospectively applicable to a wide variety of other organic compounds combined with TBP. Furthermore, TBP and its associated organic co-contaminants are effectively degraded in an environmentally safe manner which avoids the use of complex equipment and substantial amounts of expensive chemical reagents.

From a technical standpoint, the method described herein is accurately characterized as a "bioremediation" process in that the foregoing waste chemicals are eliminated through the metabolic processes of a unique and newly-discovered bacteria which is combined with the chemicals and allowed to incubate. This bacteria will now be described in detail as follows:

Acinetobacter sp. ATCC 55587 Bacteria

A key aspect of the present invention is the specific bacteria used in the foregoing bioremediation process. This bacteria is a unique, newly-discovered organism which has been identified as a member of the genus Acinetobacter. Morphologically, Acinetobacter sp. (ATCC 55587) bacteria are gram negative, aerobic, rod-shaped, oxidase-negative, and catalase-positive (in accordance with catalase testing procedures outlined in Gerhart, J. (ed.), *Manual of Methods for General Bacteriology*, American Society of Microbiology, Washington, D.C. (section therein entitled, "General Characterization", pp. 411–442 (1981) by Smibert, R. M., et al.). Furthermore, the organism has polar fimbrae determined using Leifson's technique as outlined in Gerhart, J. (ed.), *Manual of Methods for General Bacteriology*, American Society of Microbiology, Washington, D.C. (section therein entitled, "Specimen Preparation for Light Microscopy", pp. 21–33 (1981) by Doetsch, R. N.). The cells of Acinetobacter (ATCC 55587) become spherical when cultivated in trypticase soy broth (hereinafter "TSB"). In addition, Acinetobacter sp. (ATCC 55587) bacteria colonies cultivated on trypticase soy agar (hereinafter "TSA") are smooth, soft, yellow-white, have a convex elevation, and are circular with an entire margin (distinct). A best-fit coefficient of 0.363 was obtained with Acinetobacter sp. (ATCC 55587) using fatty-acid analysis (performed by Microbial ID, Inc. of Newark, Del. (U.S.A.)) and a coefficient of 0.693 was obtained with Acinetobacter genospecies 11 using GN Microplates obtained from Biolog, Inc. of Hayward, Calif. (U.S.A.).

Acinetobacter sp. (ATCC 55587) bacteria may be found in soil materials contaminated with petroleum products. In this regard, Acinetobacter sp. (ATCC 55587) bacteria has been demonstrated to effectively metabolize (degrade) commercial oil materials composed of heavy dewaxed paraffinic alkanes. These oil materials may be used by Acinetobacter sp. bacteria as growth substrates notwithstanding the presence of additional compositions combined therewith including but not limited to antioxidants and rust inhibitors. Acinetobacter sp. (ATCC 55587) was first isolated from oil-contaminated soil at an abandoned petroleum dealer/service station located between 3750 and 3810 N. Yellowstone Highway (Highway 26) in Idaho Falls, Id. (U.S.A.). Additional quantities of the organism may be obtained at this location and prospectively at other locations having substantial amounts of oil-contaminated soil.

In order to initially obtain a biologically pure culture of Acinetobacter sp. (ATCC 55587) bacteria (which is a key aspect of the present invention), a number of steps were taken as described herein. First, 1.0 g of soil obtained from the above-cited location in Idaho Falls, Id. (U.S.A.) was added to 100 ml of liquid salts medium which consisted of (on a per liter basis) about 2.0 g $Na_2SO_4$; 2.0 g $MgSO_4.7H_2O$; 0.5 g $K_2HPO_4$; 1.0 g $NH_4Cl$; and 2.0 g $KN_3$. As a growth substrate, turbine oil manufactured and sold under the name Regal™ by Texaco Lubricants Company, a Division of Texaco Refining and Marketing, Inc. of Houston, Tex. (U.S.A.) was initially added to the salts medium. The salts medium was ultimately formulated to include 1.0% by volume turbine oil.

The medium/soil mixture was then incubated for 1 week at room temperature (about 22–25° C.) with agitation using a conventional rotary shaker unit. Thereafter, a 1.0 ml aliquot of the mixture was subcultured which involved aseptic transfer into 100 ml of a salts medium containing (on a per liter basis) 5.24 g $Na_2HPO_4$; 0.25 g $MgSO_4.7H_2O$; 2.77 g $K_2HPO_4$; and 0.5 g $NH_4Cl$. In addition, turbine oil of the type set forth above was added so that the subculture medium contained about 10% by weight oil. When the subculture became turbid (e.g. cloudy) within 2–3 days, a sample of the subculture was conventionally streaked onto TSA (defined above) which is commercially available from Becton-Dickinson, Inc. of Cockeysville, Md. (U.S.A.). The isolated, biologically pure cultures of Acinetobacter sp. BGL1a bacteria obtained from the foregoing step were ultimately maintained on TSA slants and transferred monthly. In addition to the foregoing TSA cultures, cultures were also maintained by yearly transfer in a salts medium of the type set forth above (e.g. containing $Na_2HPO_4$, $MgSO_4.7H_2O$, $K_2HPO_4$, and $NH_4Cl$) which further contained about 1.0 ml of a mixture having about 10 parts TBP and about 90 parts dodecane.

The Bioremediation Process Using Acinetobacter Bacteria

In order to treat liquid mixed wastes containing TBP in combination with other non-TBP organic compounds, the liquid mixed wastes are physically combined with a supply of Acinetobacter sp. bacteria. Specifically, a biologically pure culture of Acinetobacter sp. (ATCC 55587) bacteria is first obtained (e.g. using the procedures set forth above.) Next, the organism is combined with liquid waste materials containing TBP in combination with various other organic compounds including but not limited to dodecane, tridecane, tetradecane, pentadecane, n-butanol, kerosene, petroleum-based oil (e.g. turbine oil), and mixtures thereof. These materials all individually function as growth substrates for the organism. As discussed below in greater detail, one or more of the organic compounds combined with the TBP must be capable of functioning as a growth substrate for the Acinetobacter sp. bacteria as determined by preliminary pilot testing. Specifically, prior to combining the bacteria with a selected liquid waste mixture, a preliminary determination is preferably made as to the types of non-TBP organic compounds therein. If necessary, preliminary pilot tests are then conducted using the basic procedures set forth below to determine if the specific organic compounds under consideration may be used by Acinetobacter sp. bacteria as growth substrates. If positive results are achieved, the process of the present invention may then be allowed to continue. If any of the organic compounds in the mixture cannot be metabolized or co-metabolized by the bacteria, they will not be degraded or substantially eliminated as noted above.

In a preferred embodiment of the present invention, the liquid waste mixture will contain up to about 10.0% by weight combined non-TBP organic compounds capable of being used by Acinetobacter sp. bacteria as growth substrates, and up to about 1.0% by weight TBP. The liquid waste mixture may or may not contain radioactive materials therein (e.g. radionuclides). weight TBP) as indicated above. Liquid waste mixtures containing considerably more than about 1.0% by weight TBP may cause bacteria growth inhibition, depending on the specific characteristics of the liquid waste mixtures being treated.

In a waste mixture containing the above-listed quantities of contaminants, the Acinetobacter sp. bacteria is added to the mixture in an amount approximately equal to about $10^5$–$10^8$ Acinetobacter sp. bacterial cells per ml of liquid waste mixture. Addition of the proper amount of bacteria is accomplished through the use of a conventional Petroff-Hauser counter system and the techniques associated therewith in which a designated quantity of bacteria-containing solution is microscopically observed to determine the number of cells per unit volume of solution. Using this information in accordance with basic and conventional mathematical calculations, the proper amount of bacteria-containing solution may then be added to the liquid waste mixture to achieve the foregoing cell count. However, the amount of Acinetobacter sp. bacteria to be used will necessarily vary, depending on the relative concentrations of contaminants in the liquid waste mixture. Accordingly, the present invention shall not be limited to the use of any specific quantities of bacteria.

After combining the Acinetobacter BGL1a bacteria with the liquid waste mixture, the bacteria/waste mixture combination is agitated and allowed to incubate (while maintaining agitation) for about 10–30 days at a sustained temperature of about 20°–30° C. Agitation may be accomplished in numerous ways, including but not limited to the use of conventional rotary shaker units which are well known in the art. After termination of the foregoing incubation period, the Acinetobacter sp. bacteria will have co-metabolized (degraded) the TBP and other metabolizable organic compounds associated therewith in the waste mixture. Specifically, through metabolic processes which are not yet fully understood, the Acinetobacter sp. bacteria is capable of eliminating about 50–95% of the TBP and about 95–100% of the metabolizable organic co-contaminants in waste mixtures having the composition characteristics set forth above. While the biological mechanisms used by Acinetobacter sp. bacteria to accomplish degradation of the foregoing materials are currently unknown, it is understood that such materials are co-metabolized as noted above. The term "co-metabolized" as used herein shall again involve a situation wherein a material which is not utilized for growth by an organism can, in fact, be metabolized when combined with another material which is a growth substrate for the organism. Specifically, in the present case, TBP is not effectively metabolized by Acinetobacter sp. bacteria (e.g. used as a sole carbon source) unless the TBP is combined with other organic materials which the bacteria can specifically use as growth substrates. Thus, the use of Acinetobacter sp. bacteria is of primary importance in situations involving mixed TBP waste materials which are normally encountered in most industrial applications (e.g. in the processing of nuclear fuels). As far as degradation of the foregoing materials by Acinetobacter sp. bacteria is concerned, the term "degradation" as used herein shall again involve a situation wherein the TBP and organic co-contaminants associated therewith are converted by the bacteria to cell mass (e.g. bacterial cellular components), fatty acids, acetic acid, and the like as noted above. These materials are essentially non-hazardous and may either be released into the environment or stored with a minimal degree of risk.

Bioreactor System for the Use of Acinetobacter sp.

Figure 1:
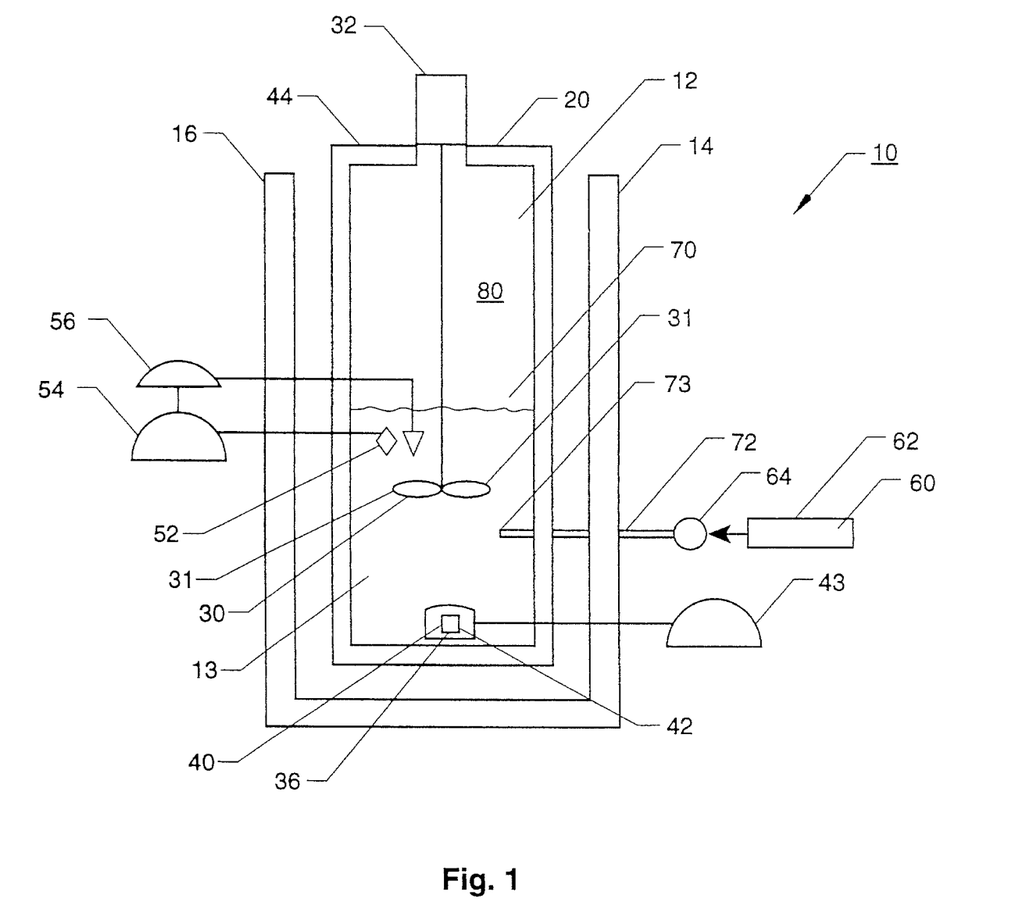
FIG. 1 is a schematic illustration of an exemplary bioreactor system suitable for implementing the process of the present invention.

In a preferred embodiment, implementation of the present invention will involve the use of a specific bioreactor system for degrading TBP and its organic co-contaminants in a liquid waste mixture. An exemplary bioreactor system is schematically illustrated in FIG. 1 and described below. It should be noted that the following discussion of a representative bioreactor system is for example purposes only. Accordingly, the invention shall not be limited to any of the specific components and materials listed below.

With reference to FIG. 1, an exemplary bioreactor system is schematically illustrated at reference number 10. The bioreactor system 10 basically includes a containment vessel 12 in the form of a tank which may be constructed of any biologically and chemically inert material (e.g. glass, stainless steel, polypropylene, or Teflon®) The containment vessel 12 (which may be of variable size) is designed to retain the Acinetobacter sp. bacteria and mixed liquid waste materials to be treated (designated in FIG. 1 by reference number 13). An exemplary, commercially-available vessel suitable for this purpose will consist of a cylindrical leak-proof tank constructed of one of the foregoing materials. In a preferred embodiment, the containment vessel 12 will be positioned within a secondary liquid containment system 14 (e.g. a basin 16 or other comparable receptacle sized to receive the containment vessel 12 therein.) The secondary liquid containment system 14 is designed to function as a receptacle for any liquid materials which may accidently leak or otherwise flow outwardly from the containment vessel 12. Also included in a preferred embodiment is radiation shielding 18 (e.g. an external lead coating/layer 20) which preferably surrounds the containment vessel 12 and is operatively attached thereto. The radiation shielding 18 is especially useful with respect to the treatment of mixed liquid waste materials having radioactive wastes therein.

A variety of basic sub-systems will optimally be associated with the containment vessel 12. For example, operatively connected to and preferably positioned within the containment vessel 12 is agitation means 30. In a preferred embodiment, the agitation means 30 will consist of a plurality of rotating blades or paddles 31 which are driven by an external (e.g. overhead) electric motor 32. Other agitation means 30 may also be used in connection with the containment vessel 12. For example, commercially available shaking devices including but not limited to conventional vibrating platforms (not shown) may be employed, as well as standard impeller systems. These systems cause axial displacement of the containment vessel 12 in a rapid, reciprocating manner. Also, a recirculating pump (not shown) may be used to continuously recirculate the bacteria and liquid waste materials into and out of the containment vessel 12, thereby causing the agitation and physical displacement of such materials. Accordingly, the present invention shall not be limited to any particular agitation means 30.

It is desirable to continuously agitate the combined bacteria and liquid waste materials so that complete degradation of the TBP and other metabolizable wastes associated therewith takes place. Also, agitation ensures that any radioactive materials which may be present within the containment vessel remain in suspension and do not cause problems.

Next, the bioreactor system 10 of the present invention will include temperature control means 36 preferably in the form of a thermostatically-controlled heater unit 40 operatively connected to or within the containment vessel 12. The heater unit 40 may involve a wide variety of types ranging from a conventional immersion type heating system 42 having an external monitoring/control unit 43 (FIG. 1) to a jacket-type electrical resistance heating unit (not shown) which entirely or partially covers the exterior surface 44 of the containment vessel 12. Accordingly, the present invention shall not be limited to any particular temperature control means 36. Components used in connection with the foregoing heating systems may be obtained from Cole-Parmer, Inc. of Chicago, Ill. (U.S.A.). As stated above, it is preferred that the Acinetobacter sp. bacteria and combined liquid mixed waste materials be maintained at an incubation temperature of about 20°–30° C. during the metabolic degradation process. The maintenance of this temperature range is important in order to ensure maximum microbial activity. As noted above, however, temperatures above 35° C. should be avoided. Such temperatures could cause substantial inhibition of microbial metabolic activity and/or cell death.

Two additional optional subsystems may also be used in connection with the bioreactor system 10 and containment vessel 12. The first of these systems involves pH control means 50 schematically illustrated in FIG. 1 which is operatively connected to and in fluid communication with the containment vessel 12. In a preferred embodiment, the pH control means 50 will consist of a pH monitor 52 operatively connected to a conventional set-point controller 54 which activates a standard delivery system 56 for pH control agents (e.g. acids and/or bases). Exemplary acid materials suitable for pH adjustment include but are not limited to mineral acids such as hydrochloric acid, phosphoric acid, sulfuric acid and nitric acid. Likewise, exemplary base materials suitable for use herein include but are not limited to sodium hydroxide and potassium hydroxide. The amount of acid and base materials to be added will necessarily depend on the degree of pH adjustment which is required. Accordingly, continuous monitoring of pH levels in a conventional manner using standard pH testing equipment will determine the quantity of pH control agents necessary for proper pH adjustment. Various components used to construct the foregoing pH control means 50 may be obtained from Cole-Parmer, Inc. of Chicago, Ill. (U.S.A.).

For numerous reasons, it is preferred that the combination of Acinetobacter sp. and liquid waste materials be continuously maintained within a pH range of about 6.5–8.5 during incubation. The maintenance of this range is important in order to ensure bacterial viability and promote the chemical precipitation of ionic metal and radioactive species. It should also be noted that various buffers may be added to the containment vessel 12 and contents thereof in order to moderate pH changes caused by the pH control means 50. Exemplary buffer materials suitable for this purpose will include sodium or potassium phosphates. The amount of buffers to be used may be determined by preliminary pilot studies involving the waste materials under consideration. The ultimate need for pH control means 50 is dependent on a variety of factors including but not limited to the type of materials in the waste mixture, as well as the quantity of such materials. An initial determination regarding the use of pH control means 50 may be accomplished through preliminary pilot studies on the liquid waste mixture prior to treatment wherein ambient pH readings are taken using a conventional pH test system. If the ambient pH of the liquid waste mixture does not fall within the foregoing optimum range, then pH control means 50 as described above may be necessary and appropriate.

Finally, a further optional subsystem associated with the bioreactor system 10 and containment vessel 12 will consist of oxygenation means 60 schematically illustrated in FIG. 1. Basically, in a preferred embodiment, the oxygenation means 60 will consist of a supply 62 of at least one oxygen-containing gas (e.g. air or pure oxygen) operatively connected to a conventional pump 4. These components are connected to and in fluid communication with the interior region 70 of the containment vessel 12 through the use of a tubular conduit 72 as illustrated in FIG. 1. The terminal end 73 of the tubular conduit 72 is preferably positioned within the interior region 70 of the containment vessel 12 so that the terminal end 73 is immersed within the bacteria and liquid waste mixture being treated. Various components used to construct the above-described oxygenation means 60 may be commercially obtained from Cole-Parmer, Inc. of Chicago, Ill. (U.S.A.).

Alternative oxygenation means 60 will include but not be limited to a membrane system which includes a plurality of tubular, commercially available gas-permeable membranes (not shown) through which oxygen-containing gas (e.g. air or pure oxygen) is passed from a pressurized source. These membranes (which are immersed within the bacteria and liquid waste mixture) enable diffusion of the oxygen-containing gas therethrough without the generation of significant amounts of bubbles, foam, and the like. In a further alternative embodiment, a selected oxygen-containing gas (e.g. pure oxygen or air) may simply be introduced into the head space 80 (FIG. 1) within the containment vessel 12. As a result, the oxygen-containing gas will diffuse (absorb) into the bacteria and liquid waste mixture at the surface thereof. Accordingly, the present invention shall not be limited to the use of any particular oxygenation means 60.

The introduction of an oxygen-containing gas into the combined bacteria/liquid waste mixture is important because Acinetobacter sp. is an aerobic organism. Specifically, the introduction of oxygen-containing gas facilitates the degradation of TBP and metabolizable organic wastes associated therewith by satisfying the respiratory requirements of Acinetobacter sp. While the amount of oxygen-containing gas to be introduced directly into the foregoing materials is not critical and may be varied, optimum results are achieved when about 20–30 cfm of gas (per 1000 $f^3$ of containment vessel volume) at a temperature of about 20°–30° C. is introduced.

Use of the bioreactor system 10 as described above and illustrated in FIG. 1 will result in effective implementation of the present invention. However, as noted herein, the invention shall not be limited exclusively to the above-listed specific components and arrangements thereof which are provided entirely for example purposes.

In order to demonstrate the various metabolic characteristics of Acinetobacter sp. (ACTT 55587) bacteria and the effectiveness thereof in degrading TBP and various metabolizable organic materials combined therewith, the following experimental three-part Example is provided as follows:

Example

Part I:

In this part of the present Example, a test was conducted to determine the ability of Acinetobacter sp. BGL1a bacteria to metabolize a petroleum-based oil product. Specifically, the test involved turbine oil sold under the name Regal™ by Texaco Lubricants Company, a Division of Texaco Refining and Marketing, Inc. of Houston, Tex. (U.S.A.). This turbine oil contained heavy dewaxed paraffinic alkanes in combination with antioxidants, antimicrobial agents, and rust inhibitors. Prior to use, the turbine oil was sterilized by filtration through 0.2 μm PFTE (e.g. Teflon®) membrane filters obtained from the Gelman Co. of Ann Arbor, Mich. (U.S.A.). To assess the growth of Acinetobacter sp. (ACTT 55587) bacteria in an environment containing the foregoing turbine oil, triplicate cultures were grown in 500 ml Wheaton bottles with PFTE lined caps. Each of the bottles contained 250 ml of a mineral salts solution combined with the foregoing turbine oil so that the solution was 1.0% by volume turbine oil. The mineral salts solution had a pH of 7.2 and contained 5.24 g $Na_2HPO_4$, 2.77 g $KH_2PO_4$, 0.50 g $NH_4Cl$, and 0.25 g $MgSO_4.7H_2O$ per liter of solution. Likewise, an equal number of 500 ml Wheaton bottles were supplied with Acinetobacter sp. (ATCC 55587) bacteria and the foregoing mineral salts solution without the above-described turbine oil (as a control).

The inoculum (grown for 24 hours in TSB obtained from Becton-Dickinson of Cockeysville, Md. (U.S.A.)) was harvested by centrifugation (13,000×g at 4° C.), washed three times and resuspended in a sterile mineral salts solution of the same type set forth above. Cultures were inoculated to a cell density of about $10^6$ cells per ml and incubated with agitation. Growth was assessed by a conventional acridine orange direct count procedure (hereinafter "AODC") as further described in greater detail below.

After the passage of 4 weeks, the residual oil was analyzed by gas chromatography. Abiotic losses were assessed with uninoculated oil-containing mineral salts medium. All oil-containing culture and control samples were extracted three times with 40 ml volumes of methylene chloride (Optima Pesticide/HPLC grade material obtained from Fisher Scientific Co. of Pittsburgh, Pa. (U.S.A.)). Extracts were concentrated to approximately 4 ml using a Kontes Kuderna-Danish apparatus (at 80°–85° C.) and then increased to a volume of 5 ml. Hexamethylbenzene was used as the internal standard (obtained from the Eastman Kodak Co. of Rochester, N.Y. (U.S.A.)).

Samples were analyzed with a Hewlett-Packard Co. (Palo Alto, Calif. (U.S.A.)) model 5890 series II gas chromatograph equipped with a 0.22 mm×25 m HT-5 column (Scientific Glass Engineering of Austin, Tex. (U.S.A.)) and a flame ionization detector. The carrier gas consisted of helium (2 ml per minute), with the injection port and detector being maintained at 225° C. and 300° C., respectively. Oven temperature was held at 150° C. for 1 minute and increased at a rate of 15° C. per minute to 270° C. The oven temperature was thereafter increased from 270° C. to 400° C. at a rate of 10° C. per minute.

It should be noted that in this part of the present Example (and in the other parts set forth below), microbial growth was assessed by AODC using a modification of the method set forth in Daley, R. J., et al., "Direct Counts of Aquatic Bacteria by a Modified Epifluorescence Technique", *Limnol. Oceanogr.*, 20:875–882 (1975). Cells were preserved with filter-sterilized formalin which was added to a final concentration of 2.0% by volume. To disrupt cell clumps and ensure a relatively uniform cell distribution during filtration, a detergent mixture was used in conjunction with sonication. The detergent mixture consisted of 0.03% Tween and 0.07% sodium pyrophosphate. The detergent mixture was added to the sample in a ratio of 1:1 and the sample sonicated for 2–3 minutes in a bath sonicator (Model #8857 manufactured by the Cole-Palmer Co. of Chicago, Ill. (U.S.A.)). Samples were filtered onto 25 mm, 0.2 μm black polycarbonate filters (available from Nucleopore, Inc. of Pleasanton, Calif. (U.S.A.) or Poretics, Inc. of Livermore, Calif. (U.S.A.)) and thereafter stained with 0.01% acridine orange for 2 minutes. A Zeiss Universal microscope model IIIRS (Carl Zeiss Co. of Oberkochen, Germany) was used for observation. The microscope had an epifluorescence illumination system (50 W halogen lamp, 450–490 nm band-pass filter, 510 nm beam splitter, and 520 nm barrier filter.)

In the remaining parts of the present Example set forth below, proteins were assayed using a method described in Peterson, G. L., "A Simplification of the Protein Assay Method of Lowery et al. which is More Generally Applicable", *Analytical Biochem.*, 83:346–356 (1977). This method involves the assessment of cell biomass by measuring cellular protein. Aliquots (1 ml) from the incubated cultures were assayed for protein concentration and compared to bovine serum albumin standards. Absorbance was measured with a spectrophotometer (produced by Bausch & Lomb of Rochester, N.Y. (U.S.A.) under the designation "Spectronics 2000") at 750 nm using the foregoing mineral salts medium as a blank.

Finally, in all parts of the present Example, deionized water was used for the preparation of media and aqueous reagents. Glassware was prepared by immersion in sulfuric acid solution containing Nochromix (from Godax Laboratories, Inc. of New York, N.Y. (U.S.A.)) and rinsed three times with deionized water.

Figure 2:
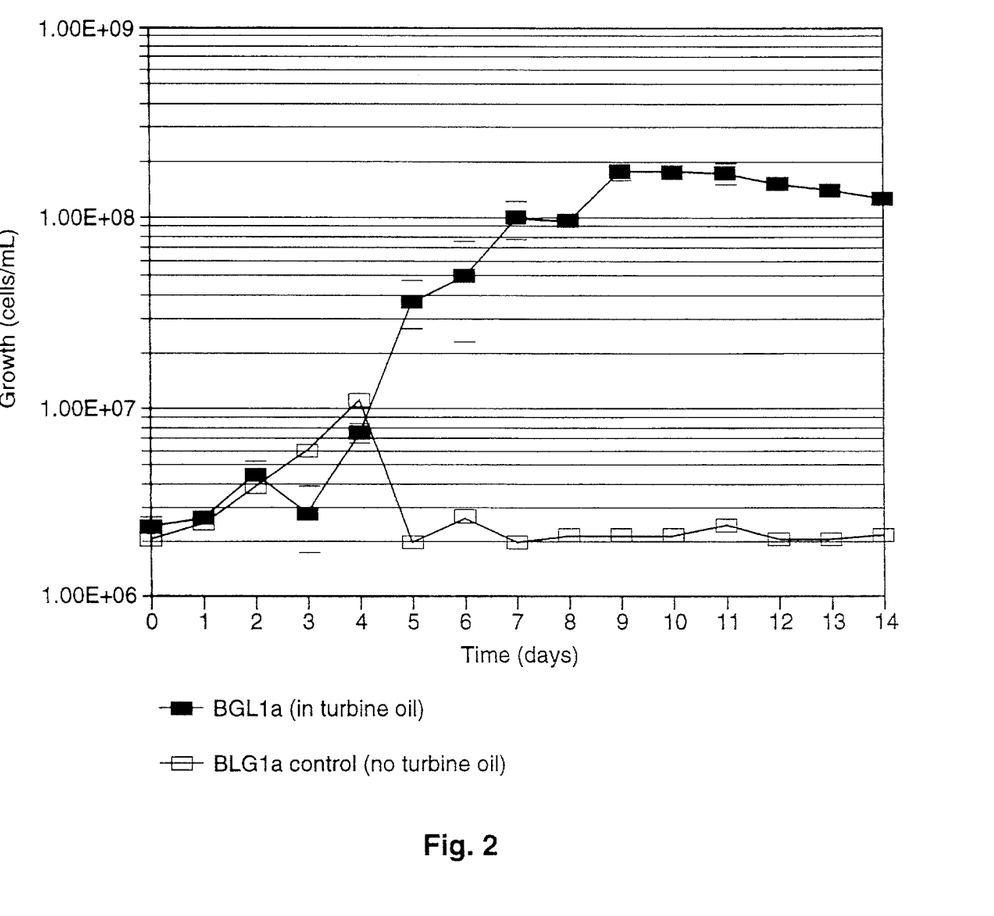
FIG. 2 is a graphic representation of the growth of Acinetobacter spa. ATCC 55587 bacteria in a medium containing turbine oil as a growth substrate.
Figure 3:
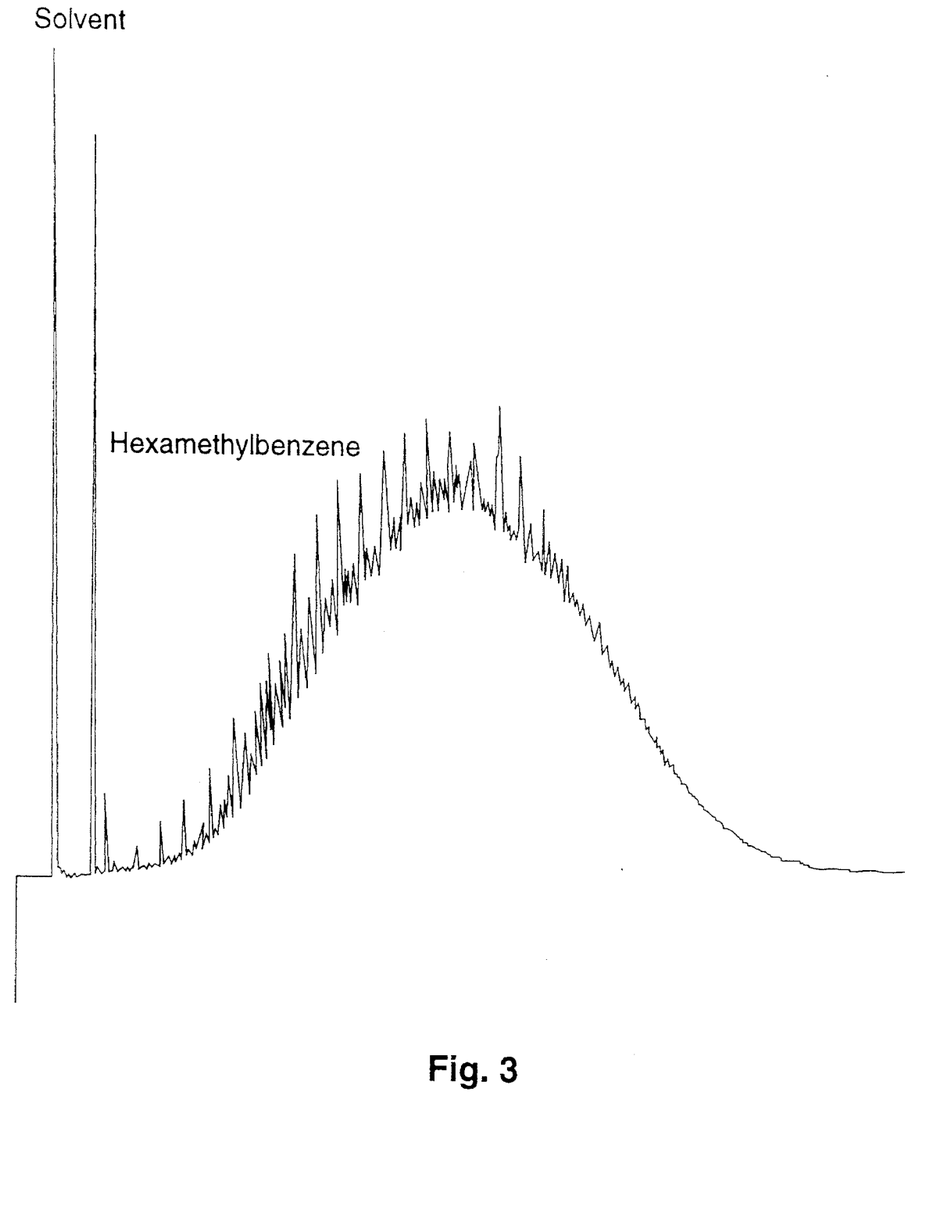
FIG. 3 is a gas chromatogram of uninoculated turbine oil in the test associated with FIG. 2.
Figure 4:
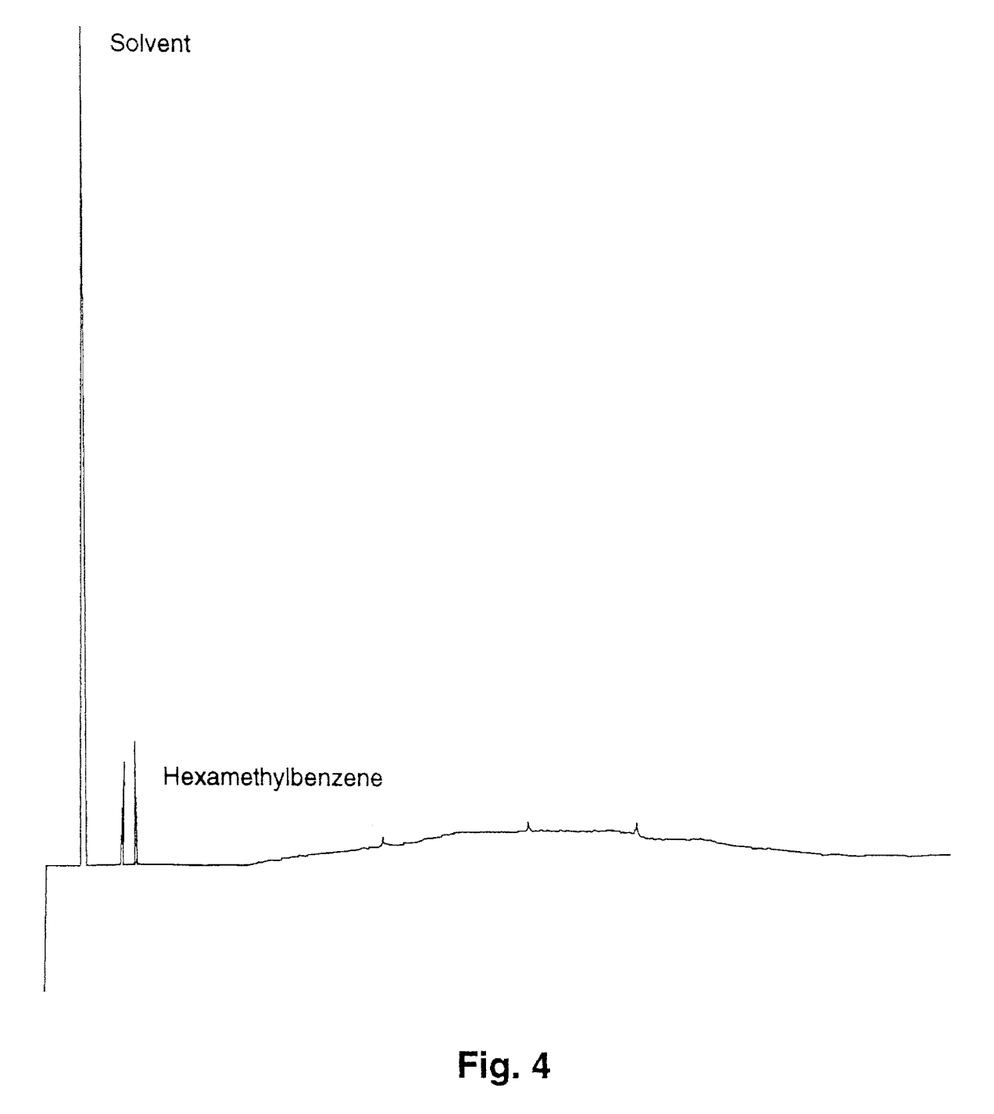
FIG. 4 is a gas chromatogram of turbine oil in the test associated with FIG. 2 after inoculation thereof with Acinetobacter sp. ACTT 55587 bacteria.

Part I Test Results:

This part of the present Example clearly indicates that Acinetobacter sp. (ATCC 55587) bacteria is capable of effectively degrading turbine oil containing heavy dewaxed paraffinic alkanes in combination with antioxidants and rust inhibitors. Specifically, with reference to FIG. 2, a graphical representation is provided which illustrates the considerable growth of Acinetobacter sp. bacteria in an oil-containing environment compared with inconsequential growth in a non-oil-containing environment. As illustrated in FIG. 2, under batch culture conditions in salts medium containing 1.0% by volume turbine oil, Acinetobacter sp. bacteria was effectively able to use the oil as a growth substrate. Cell densities specifically increased from $10^6$ cells per ml at inoculation to $10^7$ cells per ml at 5 days and $10^8$ cells per ml after 10 days of incubation. With continued reference to FIG. 2, in a salts medium without oil therein, cell densities of $10^7$ cells per ml were obtained. This small degree of growth was due to the utilization of trace organic materials, nutrient carryover or endogenous reserves. In addition, the gas chromatographic analyses of the extracted mineral salts medium containing turbine oil indicated that extensive degradation of the turbine oil occurred within the fourteen day incubation period. Specifically, FIGS. 3 and 4 illustrate gas chromatograms of uninoculated and inoculated turbine oil, respectively. The differences in these gas chromatograms are highly significant, especially with respect to FIG. 4 which involves the above-described turbine oil fourteen days after inoculation with Acinetobacter sp. bacteria.

Part II:

In this part of the present Example, the growth of Acinetobacter sp. (ATCC 55587) bacteria in a mixture of alkanes and TBP was studied. The inoculum (grown for 24 hours in TSB) was harvested by centrifugation as previously described in Part I, washed three times, and resuspended in a sterile mineral salts solution of the same type described in Part I. Cultures were inoculated to a cell density of about $10^6$ cells per ml into 100 ml of the same type of mineral salts medium listed in Part I. These materials were placed in multiple 250 ml Erhlenmeyer flasks fitted with PFTE-lined screw caps. However, in this part of the present Example, the mineral salts medium contained dodecane, tridecane, tetradecane, pentadecane, and TBP (all obtained from the Aldrich Chemical Co., Inc. of Milwaukee, Wis. (U.S.A.)). The concentration of each of these ingredients was 200 μg per ml of medium. To assess abiotic degradation or volatilization of the foregoing components, an equal number of flasks were prepared which contained the foregoing mineral salts medium and the above-listed organic additives. The flasks were thereafter incubated at 30° C. with agitation. On each sampling day, triplicate flasks were analyzed for cell numbers as determined by AODC (described above). Likewise, biomass was analyzed by protein determination as previously discussed in Part I, and the degradation of organic materials was determined by gas chromatography. Aliquots were removed for cell enumeration and biomass determination, with the remainder of each flask being extracted for gas chromatographic analysis of residual organic materials.

To prepare samples for gas chromatographic analysis, cultures were extracted three times with 20 ml volumes of methylene chloride using hexadecane as the extraction standard, with the extracts thereafter being brought to proper volume. The temperature program used was 80° C. for 1 minute with a subsequent increase to 140° C. at a rate of 20° C. per minute. The oven temperature was increased from 140° C. to 200° C. at a rate of 10° C. per minute and held for 1 minute at 200° C. The injection port and detector were held at 175° C. and 200° C., respectively.

Figure 5:
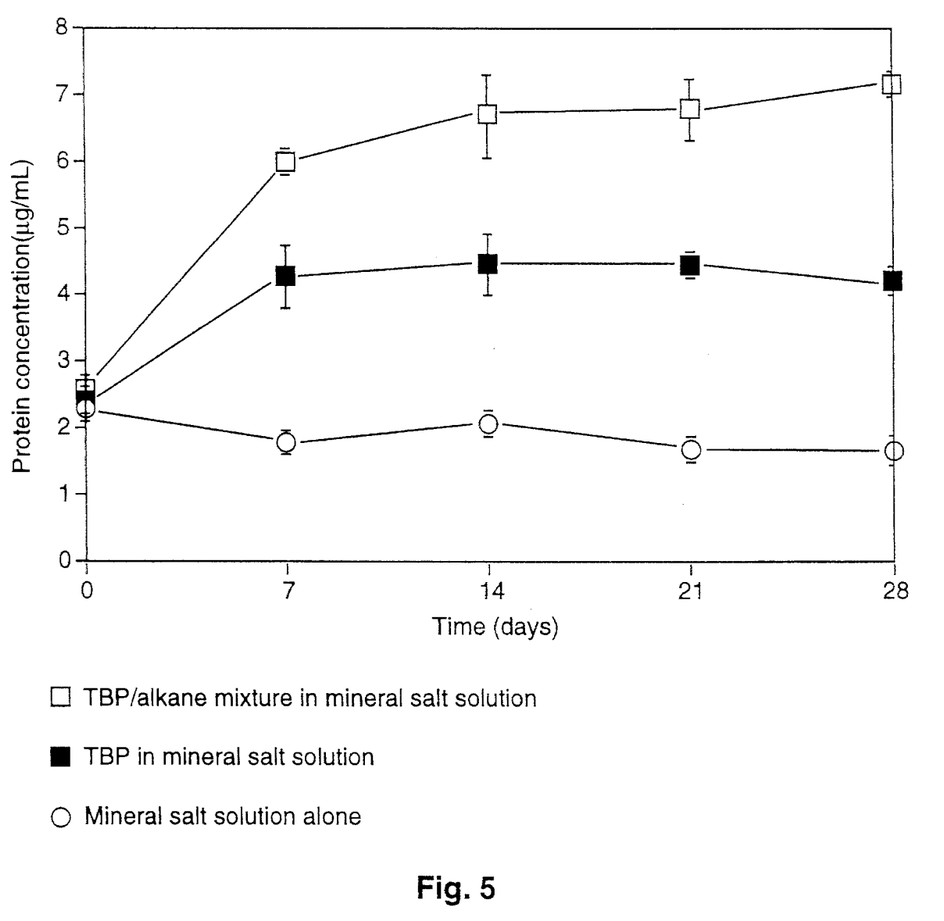
FIG. 5 is a graphic representation of total protein concentration during a 28 day period in a test involving the growth of Acinetobacter sp. ATCC 55587 bacteria in a medium containing TBP and a plurality of alkanes.
Figure 6:
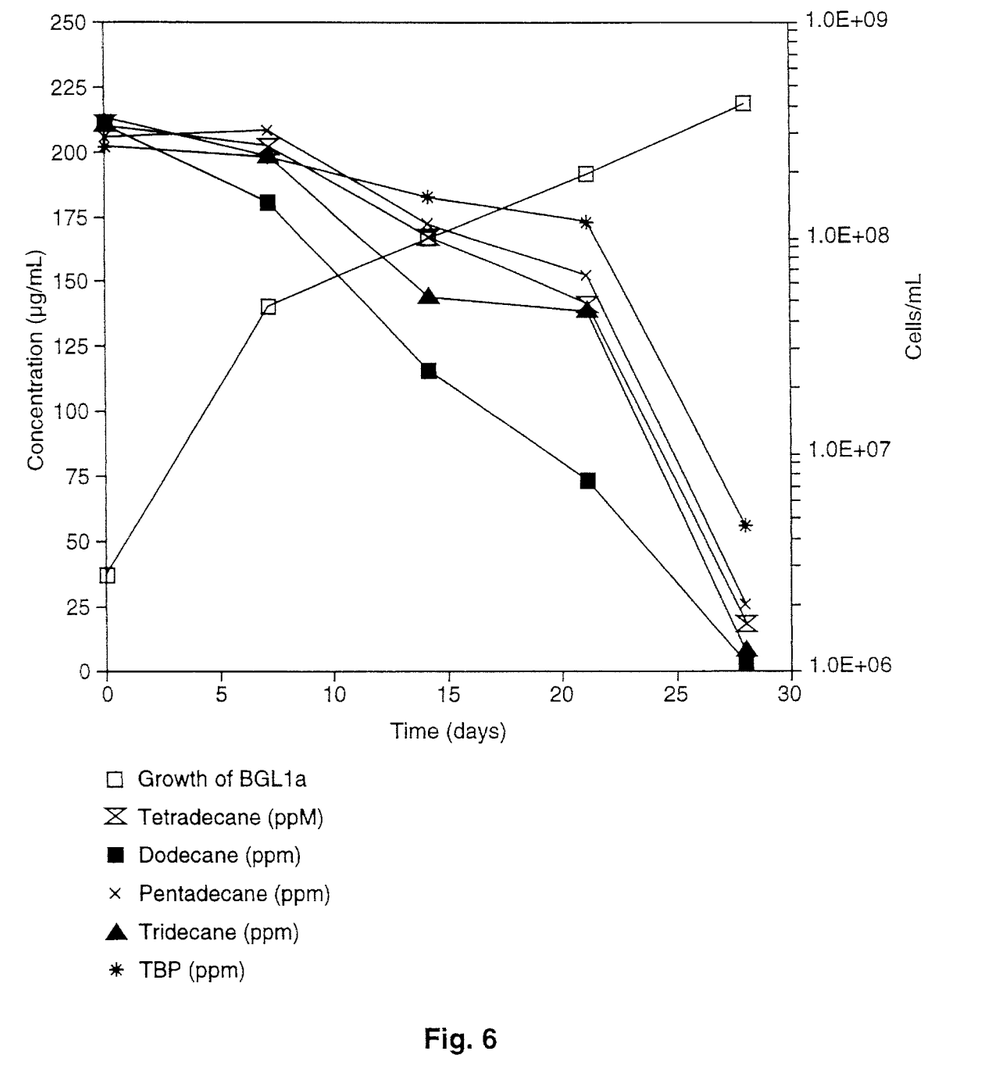
FIG. 6 is a graphic representation illustrating the degradation by Acinetobacter sp. ATCC 55587 bacteria of the components in a medium containing TBP and a plurality of alkanes.

Part II Test Results:

The results of Part II clearly indicate that Acinetobacter sp. bacteria co-metabolized and degraded each component of a chemical mixture containing dodecane, tridecane, tetradecane, pentadecane, and TBP as described above. Cell densities in the foregoing cultures increased from $10^6$ cells per ml to $10^8$ cells per ml. During early log phase, cells were larger than those in mid to late log phase. Due to this difference, biomass was assessed by cellular protein measurement. Most of the biomass was produced during the first seven days as illustrated in the graph of FIG. 5. Initially, the organic components of the foregoing mixture were degraded at different rates. The order of degradation rates for the first 21 days of incubation was as follows: dodecane>tridecane>tetradecane=pentadecane>TBP. By the end of the 28 day incubation period, greater than 90% of the above-listed alkane components had been degraded, while 75% of the TBP was degraded as illustrated in the graph of FIG. 6 (which involves time v. ingredient concentration and cells/ml as determined by chromatographic analysis and the other techniques set forth above). No abiotic losses of the alkanes or TBP were observed in the control flasks. By day 28, less than 10% of the original TBP/alkane mixture remained. Accordingly, these results clearly demonstrate the ability of Acinetobacter sp. (ATCC 55587) bacteria to effectively co-metabolize (degrade) TBP in combination with a plurality of metabolizable organic compounds.

Part III:

In this part of the present Example, the growth/metabolic characteristics of Acinetobacter sp. (ATCC 55587) bacteria in a media environment containing only TBP were analyzed. The inoculum and methods used in this part of the present Example were the same as those listed above in Part II with one exception. Specifically, the mineral salt solutions did not contain any of the above-listed alkane materials, and instead only included 200 μg of TBP per ml of solution.

Part III Test Results:

Acinetobacter sp. bacteria did not utilize TBP as a growth substrate. This result indicates that the degradation of TBP in a mixture containing other organic components (as described in Part II) occurs via a co-metabolic process.

As indicated above, the present invention represents a considerable advance in the art of hazardous waste treatment. Specifically, newly-discovered Acinetobacter sp. bacteria is capable of co-metabolizing (degrading) mixtures of waste materials which include TBP as well as numerous other organic compounds (e.g. alkanes). The waste treatment method described herein is safe, effective, cost-efficient, and avoids the use of complex equipment and large amounts of expensive chemical reagents. For this reason, the methods and materials of the present invention satisfy a long-felt need in the field of waste treatment technology.

Having described herein preferred embodiments of the present invention, it is anticipated that suitable modifications may be made thereto by individuals skilled in the art which nonetheless remain within the scope of the invention. Accordingly, the present invention shall only be construed in conjunction with the following claims:

The invention that is claimed is:

1. A method for the degradation of tributyl phosphate in a liquid waste mixture comprising the steps of:

providing a supply of Acinetobacter genospecies 11 bacteria;

providing a liquid waste mixture comprising tributyl phosphate and at least one organic compound capable of being utilized by said Acinetobacter genospecies 11 bacteria as a growth substrate;

combining said Acinetobacter genospecies 11 bacteria, in an amount effective to degrade said tributyl phosphate, with said waste mixture; and allowing said Acinetobacter genospecies 11 bacteria to metabolize and degrade said tributyl phosphate and said organic compound within said waste mixture under conditions and for a time sufficient for the degradations to occur.

2. The method of claim 1 wherein said waste mixture comprises up to about 1.0% by weight said tributyl phosphate.

3. The method of claim 1 wherein said organic compound is selected from the group consisting of dodecane, tridecane, tetradecane, pentadecane, n-butanol, kerosene, turbine oil, and mixtures thereof.

4. The method of claim 1 wherein said waste mixture comprises up to about 10.0% by weight said organic compound.

5. The method of claim 1 wherein said Acinetobacter genospecies 11 bacteria is added to said waste mixture in an amount equal to about $10^5$–$10^8$ cells of said Acinetobacter genospecies 11 bacteria per ml of said waste mixture.

6. The method of claim 1 wherein said allowing of said Acinetobacter genospecies 11 bacteria to metabolize and degrade said tributyl phosphate and said organic compound within said waste mixture occurs over a period of about 10–30 days.

7. The method of claim 1 wherein said Acinetobacter genospecies 11 bacteria and said waste mixture are maintained at a temperature of about 20°–30° C. after said combining thereof.

8. The method of claim 1 further comprising the step of agitating said Acinetobacter genospecies 11 bacteria and said waste mixture after said combining thereof.

9. The method of claim 1 further comprising the step of introducing at least one oxygen-containing gas into said Acinetobacter genospecies 11 bacteria and said waste mixture after said combining thereof to provide oxygen conditions sufficient for the degradations to occur.

10. The method of claim 1 further comprising the step of adding at least one pH control agent to said Acinetobacter genospecies 11 bacteria and said waste mixture after said combining thereof to provide pH conditions sufficient for the degradations to occur.

11. A method for the degradation of tributyl phosphate in a liquid waste mixture comprising the steps of:
- providing a supply of Acinetobacter genospecies 11 bacteria;
- providing the a liquid waste mixture comprising up to about 1.0% by weight tributyl phosphate and up to about 10.0% by weight of at least one organic compound capable of being utilized by said Acinetobacter genospecies 11 as a growth substrate;
- combining said Acinetobacter genospecies 11 bacteria, in an amount effective to degrade said tributyl phosphate, with said waste mixture; and
- allowing said Acinetobacter genospecies 11 bacteria to metabolize and degrade said tributyl phosphate and said organic compound within said waste mixture under conditions and for a time sufficient for the degradations to occur.

12. The method of claim 11 wherein said organic compound is selected from the group consisting of dodecane, tridecane, tetradecane, pentadecane, n-butanol, kerosene, turbine oil, and mixtures thereof.

13. The method of claim 11 wherein said allowing of said Acinetobacter genospecies 11 bacteria to metabolize and degrade said tributyl phosphate and said organic compound within said waste mixture occurs over a period of about 10–30 days.

14. The method of claim 11 wherein said Acinetobacter genospecies 11 bacteria and said waste mixture are maintained at a temperature of about 20°–30° C. after said combining thereof.

15. The method of claim 11 further comprising the step of agitating said Acinetobacter genospecies 11 bacteria and said waste mixture after said combining thereof.

16. A method for the degradation of tributyl phosphate in a liquid waste mixture comprising the steps of:
- providing a supply of Acinetobacter genospecies 11 bacteria;
- providing a liquid waste mixture comprising up to about 1.0% by weight tributyl phosphate and up to about 10.0% by weight of at least one organic compound capable of being utilized by said Acinetobacter genospecies 11 bacteria as a growth substrate, said organic compound being selected from the group consisting of dodecane, tridecane, tetradecane, pentadecane, n-butanol, kerosene, turbine oil, and mixtures thereof;
- combining an amount of said Acinetobacter genospecies 11 bacteria with said waste mixture, said amount effective to degrade said tributyl phosphate and equal to about $10^5$–$10^8$ cells of said Acinetobacter genospecies 11 bacteria per ml of said waste mixture;
- agitating said Acinetobacter genospecies 11 bacteria and said waste mixture after said combining thereof; and
- allowing said Acinetobacter genospecies 11 bacteria to metabolize and degrade said tributyl phosphate and said organic compound within said waste mixture over a period of about 10–30 days at a temperature of about 20°–30° C. under pH conditions sufficient for the degradations to occur.

17. The method of claim 16 further comprising the step of introducing at least one oxygen-containing gas into said Acinetobacter genospecies bacteria and said waste mixture after said combining thereof in an amount sufficient to maintain the degradation activity of said bacteria; and
- adding at least one pH control agent to said Acinetobacter genospecies 11 bacteria and said waste mixture after said combining thereof in an amount sufficient to maintain a pH at which said degradation will occur.

* * * * *